United States Patent
Missbichler

(10) Patent No.: US 9,144,602 B2
(45) Date of Patent: Sep. 29, 2015

(54) TREATMENT OF FRUCTOSE MALABSORPTION

(75) Inventor: Albert Missbichler, Vienna (AT)

(73) Assignee: SCIOTEC DIAGNOSTIC TECHNOLOGIES GMBH, Tulln (AT)

( * ) Notice: Subject to any disclaimer, the term of this patent is extended or adjusted under 35 U.S.C. 154(b) by 191 days.

(21) Appl. No.: 13/062,414

(22) PCT Filed: Aug. 19, 2009

(86) PCT No.: PCT/AT2009/000314
§ 371 (c)(1),
(2), (4) Date: Mar. 4, 2011

(87) PCT Pub. No.: WO2010/025483
PCT Pub. Date: Mar. 11, 2010

(65) Prior Publication Data
US 2011/0165231 A1    Jul. 7, 2011

(30) Foreign Application Priority Data

Sep. 4, 2008 (AT) .................................. A 138/2008
Sep. 4, 2008 (EP) ...................................... 08450128

(51) Int. Cl.
*A61K 38/52* (2006.01)
*A61K 33/32* (2006.01)

(52) U.S. Cl.
CPC ............. *A61K 38/52* (2013.01); *A61K 33/32* (2013.01); *C12Y 503/01005* (2013.01)

(58) Field of Classification Search
CPC ...................................................... C12N 9/92
See application file for complete search history.

(56) References Cited

U.S. PATENT DOCUMENTS

| 3,847,740 A | 11/1974 | Heady et al. |
| 4,699,882 A * | 10/1987 | Visuri .................. 435/188 |
| 5,437,993 A | 8/1995 | Visuri |

FOREIGN PATENT DOCUMENTS

| DE | 102006013624 | 5/2007 |
| DE | 10 2007 008 664 | 8/2008 |
| DE | 10 2007 008 664.8 | 8/2008 |
| EP | WO 2007/059956 * | 5/2007 ............ A61K 38/54 |
| WO | 91/05857 A1 | 5/1991 |
| WO | WO 91/05857 | 5/1991 |
| WO | WO 01/12834 | 2/2001 |
| WO | 03/099410 A1 | 12/2003 |
| WO | WO 03/099410 | 12/2003 |
| WO | WO 2007/057749 | 5/2007 |
| WO | WO/2008/101672 * | 8/2008 |

OTHER PUBLICATIONS

Simren et al., Use and abuse of hydrogen breath tests., Gut (2006), vol. 55(3), pp. 297-303.*
Yamanaka et al., Purification, Crystallization and Properties of the D-xylose isomerase from *Lactobacillus brevis*., Biochimica Et Biophysica Acta (1968), vol. 151, pp. 670-680.*

(Continued)

*Primary Examiner* — Alexander Kim
(74) *Attorney, Agent, or Firm* — Norton Rose Fulbright US LLP

(57) ABSTRACT

The present invention relates to the composition comprising crystalline xylose-isomerase (EC 5.3.1.5) and at least one salt of a metal and/or alkaline earth metal.

15 Claims, 4 Drawing Sheets

(56) References Cited

OTHER PUBLICATIONS

Whitlow et al., A Metal-Mediated Hydride Shift Mechanism for Xylose Isomerase Based on the 1.6 Å *Streptomyces* rubiginosus Structure With Xylitol and D-Xylose, Proteins: Structure, Function, and Genetics (1991), vol. 9, pp. 153-173.*

Weber, Overview of Crystallization Methods. Methods in Enzymology, 1997, vol. 276, pp. 13-22.*

Drenth, "Principles of Protein X-Ray Crystallography", 2nd Edition, 1999, Springer-Verlag New York Inc., pp. 1-21.*

Klyushnichenko, Protein crystallization: From HTS to kilogram-scale, Curr. Op. Drug Discovery, 2003, vol. 6(6), pp. 848-854.*

Yang et al., Crystalline monoclonal antibodies for subcutaneous delivery, PNAS Jun. 10, 2003, vol. 100, pp. 6934-6939.*

Suzuki et al. High-Pressure Acceleration of the Growth Kinetics of Glucose Isomerase Cystals., J. Phys. Chem. (2005), vol. 109, pp. 3222-3226.*

Pastinene et al., Cross-linked glucose isomerase crystals as a liquid chromatographic separation material, Enzyme and Microbial Technilogy (2000), vol. 26, pp. 550-558.*

Dauter et al. Refinement of Glucose Isomerase from *Streptomyces albus* at 1.65 Å with Data from an Imaging Plate., (Acta Cryst. (1990), vol. B46, pp. 822-841.*

Suzuki et al. High-Pressure Acceleration of the Growth Kinetics of Glucose Isomerase Crystals., J. Phys. Chem. (2005), vol. 109, pp. 3222-3226.*

Carrell et al., "X-ray analysis of D-xylose isomerase at 1.9 A: native enzyme in complex with substrate and with a mechanism-designed inactivator," *PNAS*, 86:4440-4444, 1989.

English Translation of International Preliminary Report on Patentability issued in PCT/AT2009/000314, dated Mar. 17, 2011.

International Search Report issued in PCT/AT2009/000314, dated Jan. 20, 2010.

Carell et al., Proc. Nat'l Acad. Sci. USA, 86(12), Jun. 1989, 4440-4444.

Yamanaka, Biochimica et Biophysica Acta, vol. 151(3), 1968, 670-680.

Item 1: Third Party Observation submitted for corresponding EP application filed Nov. 19, 2011.

Item 2: Amended Claims and cover letters submitted for corresponding EP application on Nov. 3, 2011.

Item 3: Third Party Observation submitted for corresponding EP application filed May 6, 2012.

Item 4: Third Party Observation submitted for corresponding EP application filed Aug. 6, 2012.

* cited by examiner

TREATMENT OF FRUCTOSE MALABSORPTION

This application is a national phase application under 35 U.S.C. §371 of International Application No. PCT/AT2009/000314 filed 19 Aug. 2009, which claims priority to European Application No. 08450128.7 filed 4 Sep. 2008 and Austrian Application No. A 1380/2008 filed 4 Sep. 2008. The entire text of each of the above-referenced disclosures is specifically incorporated herein by reference without disclaimer.

The present invention relates to a composition for the treatment of fructose-malabsorption.

Fructose (formerly also called laevulose) belongs as monosaccharide (simple sugar) to the carbohydrates. Fructose is a widespread kind of sugar in human foodstuffs.

Fructose is present as free hexose, in household sugar (cane sugar and beet sugar) as disaccharide saccharose bound to glucose and in polymerized form as indigestible fructane. Free fructose is increasingly used in the food sector because of its sweetness intensity, which is approximately 20% higher than the one of normal sugar, and its better transportability.

In contrast to glucose, fructose is not actively absorbed in the intestine, but is passively resorbed by special proteins at a substantially slower rate. Nearly half of the population is not able to resorb more than 25 g of fructose per day. The average daily consumption, however, is between 11 g and 54 g per day. Here it has to be noted that the major part of fructose is consumed with soft drinks, which have an increasing importance in the average food intake. In addition, the increasing use of HFCS ("high fructose corn syrups") as sweetener aggravates the problem.

This malabsorption results in a disorder of the osmotic balance and, in addition, a rapid degradation by bacteria in the colon. On the one hand this leads to a troublesome formation of gas in the abdomen, an impairment of the colon motility and at medium term to a change in the bacterial population. The consequence may be a clinically manifested irritable bowel syndrome.

According to the state of the art a fructose-malabsorption is diagnosed by a fructose provocation followed by the determination of the $H_2$ content in the respiratory air. The specificity of this test lies far below 50%.

Up to now only a dietetic treatment has been available for therapy, which, however, due to the above mentioned widespread use of fructose was very difficulty to observe by the user. In addition, the avoidance of fruits leads to deficiency symptoms, which have to be compensated.

The uptake of carbohydrates in the small intestine is based on the hydrolytic cleavage by hydrolases in the intestinal lumen and on the intestinal mucosa into hexose-monosaccharides, glucose, galactose and fructose, which are then resorbed by the intestinal epithelium. For the main part this resorption is effected by three transportation proteins: SGLT1, GLUT5 and GLUT2.

SGLT1 (sodium/glucose co-transporter) acts in the ciliated border of the small intestinal epithelium. SGLT1 transports glucose and galactose against a concentration gradient, in particular with a low glucose concentration in the intestinal lumen.

GLUT5 is specific for fructose and a so-called facultative transporter. Thus, GLUT5 is strongly dependent on a concentration gradient between intestinal lumen and blood circulation. GLUT5 is present in the whole intestinal wall.

Finally, GLUT2 is a low-affinity facultative transporter of glucose, fructose and galactose. GLUT2 is obviously quickly and reversible integrated into the intestinal wall with SGLT1-activity. The activity of GLUT2 depends on multiple factors and is therefore often designed as "diffusional pathway".

Fructose-malabsorption may have different consequences.

Fructose and fructane as small molecules aggregate large amounts of water around them and transport the same into the distal small intestine and finally into the colon. This causes an acceleration of the intestinal transfer, an effect which is used in laxatives.

Fructose, transported into the colon, is quickly converted into short-chain fatty acids by the bacteria present in the host. Here large amounts of hydrogen, $CO_2$ and sometimes even methane are formed. The short-chain fatty acids have an influence on the pH value of the intestine and also provide for a higher motility.

Some bacteria use fructose for the generation of fructanes, which serve as adhesion factors to the intestinal wall. The influence of these, finally adherent, bacteria is manifold and controversial. In rats an increased epithelium proliferation and excessive mucine secretion were observed, which is normally associated with an irritation of the mucosa.

In addition, fructose-malabsorption is also associated with depressions, as the amount of tryptophane, the precursor of serotonin, in the blood circulation is influenced as well.

The influence of fructose-malabsorption on the development of gastro-intestinal disorders was first recognized in 1978 (Andersson DE, Nygren A: Acta Med Scand 1978; 203:87-92). Nevertheless—and maybe because of a lacking specific and sensitive diagnostic method—fructose-malabsorption has not been recognized generally as a disease up to now. This is also clear, as there are absorption disorders of different severity and the shift from "normal" to "pathologic" is subject to very strong individual variations.

Fructose does not only present a problem with fructose-malabsorption, but also in the hereditary fructose intolerance, both clinical pictures being summarized sometimes in the literature as fructose intolerance. Intolerance of fructose appears with a frequency of approximately 1:20.000. This is an autosomal-recessive inherited disorder of the fructose metabolism, where fructose can either be not degraded at all or not in sufficient amounts. This results in an increased fructose content in the cells having toxic effect, which affects the metabolism of glucose. The consequence is hypoglycemia.

Fructose-malabsorption may only be treated with strict low fructose or fructose-free diets. Any unbalanced diet, in particular lacking fruits, fruit juices, etc., often leads to deficiency symptoms, having a negative effect on the health status of the patient. In order to prevent any deficiencies, additional products, such as vitamin preparations, have to be taken by the patients in combination with a strict diet. Therefore all persons concerned as well as the health system must be interested in providing a form of therapy, which is affordable for a broad class of population.

In WO 2007/057749 preparations are described, which are based on the use of 5-D-fructose-dehydrogenase (EC 1.1.1.124; FDH). This enzyme changes fructose in such a way that it can no longer be used as substrate by bacteria in the gastro-intestinal tract, and therefore can no longer cause any disorders. For ameliorating the effect of FDH the addition of xylose-isomerase is suggested.

In DE 102006013624 xylose-isomerase is generally described as a means for the conversion of fructose into glucose.

In BHOSALE, S. G. et al. (Microbiol Rev 60(2), (1996): 280-300) the importance of alkaline earth metal salts for the activity of xylose-isomerase is discussed among others.

In WO 91/05857 A a method for the crystallization of enzymes, such as glucose-isomerase, is described. Furthermore this document shows, that during the crystallization of enzymes bivalent salts, such as magnesium sulfate, may be used.

WO 01/12834 A relates, among others, to a composition, which comprises cross-linked crystalline xylose-isomerase and is contacted with magnesium sulfate in the course of the substrate conversion.

In U.S. Pat. No. 3,847,740 A a composition is disclosed, which comprises xylose-isomerase and magnesium carbonate.

In WO 03/099410 A a method for the separation and purification of nucleosides is described, in which cross-linked crystalline xylose-isomerase is used.

In Carrell H. L. et al., PNAS, 86(12)(1989): 4440-4444 the x-ray structure of xylose-isomerase is disclosed. In addition, the authors state that bivalent metal ions, such as magnesium, are required for the catalytic activity of xylose-isomerase.

It is the object of the present invention to provide means, which in the case of fructose-malabsorption are able to prevent the entry of fructose into the colon, in order to suppress or significantly reduce any developing disease symptoms. Thus, the patients suffering from such a disease may continue to live a largely "normal" life, without having to abstain from fructose-containing foodstuffs.

The present invention relates to a composition, comprising crystalline xylose-isomerase (EC 5.3.1.5) and at least one salt of a metal and/or alkaline earth metal for the treatment of fructose-malabsorption.

Surprisingly it has been found that xylose-isomerase in crystalline form and in the presence of salts of metal and/or alkaline earth metals has a high activity as compared with xylose-isomerase produced in the traditional way. The crystalline form of xylose-isomerase also has the advantage that the enzyme is protected, for example, from any acidic influence in the stomach and proteases, if the crystalline xylose-isomerase is cross-linked. Cross-linkage may be reached by established methods (e.g. Vallejo-Becerra et al. (J Agric Food Chem. 2008, Feb. 7; 56(4): 1392-1397) or Wenzel et al. (FEBS Lett. 1991, Mar. 11; 280(1): 147-151). Therefore xylose-isomerase might be given in an oral administration optionally without or with a reduced enteric coating.

The xylose-isomerase or the composition is preferably in the form of a dried, fine granular powder, which preferably has been crystallized in the presence of metal ions as co-factors, in order to ensure a rapid bioavailability and high specific activity. The crystals of xylose-isomerase may be finely ground in a mill. This kind of preparation leads to a maximum activity in the physiological environment of the intestine and a quick release based on the very good solubility in the intestinal lumen.

Surprisingly, the activity and bioavailability could be increased by multiples with the help of the xylose-isomerase preparation of the invention. It was demonstrated on subjects that this high activity and efficiency prevented the entry of fructose into the colon substantially or completely. The quicker resorption of glucose in the intestinal region retracts glucose permanently from the balance reaction (fructose<->glucose) and therefore fructose is degraded in the course of time. This prevents any excessive fructose from remaining in the intestinal region, which might lead to the known health disorders based on fructose-malabsorption and subsequently to the symptoms of fructose-malabsorption.

Xylose-isomerase is used on a large industrial scale in the food industries for the preparation of fructose from glucose, in order to enhance the degree of sweetness. Under the environmental parameters in the small intestine (i.e., retraction of glucose from the balance reaction) the activity of xylose-isomerase prepared according to the invention is pushed into the other direction: The enzyme isomerizes fructose into glucose. But industrially used enzyme contains large amounts of interfering substances, which inhibit the activity of the enzyme in a decisive way, in particular of sorbitol. In contrast to the enzyme industrially used, the sorbitol content of the crystalline xylose-isomerase of the invention is <1%. Due to a sorbitol content of less than 1% the composition of the invention may reach a notable increase in activity. The impairment of stability, which was feared in the absence of sorbitol, surprisingly turned out to be incapable to affect the improved functionality of the invention decisively.

As support of xylose-isomerase also mannose-isomerase may be used for the conversion of fructose into mannose. This is also resorbed in the small intestine, as explained above, and therefore also retracted from the reaction balance.

The crystallization of xylose-isomerase is made according to the methods known already in the state of the art (Suzuki Y et al., J Phys Chem B. 109(8) 2005: 3222-6; Dunlop K V and Hazes B, Acta Crystallogr D Biol Crystallogr. 61 2005: 1041-8; Vilonen K M et al., Biotechnol. Prog. 20(5) 2004: 1555-60; Ramagopal U A et al., Acta Crystallogr D Biol Crystallogr. 59 2003: 868-75.

For reaching a high enzyme activity in the intestinal region, in particular in the small intestine, the composition comprises at least one physiologically acceptable salt of a metal and/or alkaline earth metal, with the metal being preferably bivalent. As xylose-isomerase in presence of metal and/or alkaline earth metal ions shows an increased enzyme activity, the respective salts are provided in the composition of the invention. In particular, xylose-isomerase is preferably co-crystallized with the above mentioned salts. Thus, co-factors may be integrated into the active centre of the enzyme in the crystals and therefore are already present in the crystal lattice (next to crystal water, and others). The ions and co-factors therefore need not be present in the reaction solution (=intestinal lumen) in addition. According to the invention the composition may comprise at least 2, at least 3, 4, 5, 6, 7, 8, 9, 10 or even at least 15 different kinds of salts of metals and/or alkaline earth metals.

According to a preferred embodiment of the present invention the alkaline earth metal is magnesium.

The composition of the invention comprises the salt of the alkaline earth metal in the composition in a molar ratio to xylose-isomerase ranging from 0.5:1 to 200:1, preferably from 5:1 to 25:1, more preferred from 12:1 to 18:1.

According to another preferred embodiment of the present invention the metal is cobalt, manganese, zinc, iron or copper, the salt of which is present in the composition in a molar ratio to xylose-isomerase ranging from 0.1:1 to 100:1, preferably from 0.5:1 to 20:1, more preferred from 3:1 to 7:1.

A pharmaceutical acceptable anion is used as anion for these salts, preferably selected from the group consisting of chloride, sulfate, carbonate, hydrogen carbonate or maleate.

According to a more preferred embodiment of the present invention the at least one salt is selected from the group consisting of $MgCl_2$, $MgSO_4$, $MgCO_3$, $Mg(HCO_3)_2$, $Mg(C_4H_2O_4)$, $CoCl_2$, $CoSO_4$, $CoCO_3$, $Co(HCO_3)_2$, $Co(C_4H_2O_4)$, $MhCl_2$, $MnSO_4$, $MnCO_3$, $Mn(HCO_3)_2$ or $Mn(C_4H_2O_4)$.

In a more preferred embodiment the composition of the invention comprises magnesium and/or cobalt salts. Most preferred are those compositions of the invention, which include Mg as well as Co salts. The combination of these two salts has been shown to be especially suited for the treatment of fructose-malabsorption.

According to a preferred embodiment of the present invention the crystals of xylose-isomerase are used as fine, dried powder. The enzyme powder is more stable against a bacterial degradation and has advantages in the manufacture when pelleting on a large technical scale, such as better dosing ability and better mixability.

The powder of xylose-isomerase preferably has a residual water content of 0.1% to 30%, more preferred of 0.5% to 10% and most preferred from 1% to 3%. The protein content of the powder is preferably 50% to 99.9%, more preferred 75% to 99.9%, most preferred 95% to 99.9%. The particle size of the powder ranges from 0.01 µm to 1000 µm, preferably from 0.1 µm to 100 µm and most preferred from 1 µm to 30 µm.

The xylose-isomerase composition prepared and made available according to the invention is preferably "highly active". This "highly active" xylose-isomerase composition has preferably an enzyme activity from 35,000 to 45,000 units per gram (total preparation). Here one unit (U) is defined as µmol per gram per hour at 37° C. (35,000 and 45,000 U correspond to 9.72 and 12.5 milli-Katal, respectively (µkat; kat=mol/s)). In contrary, xylose-isomerase from a lyophilisate or e.g. directly purified from a column, has an activity from about 4000 to 6000 U/g (determined according to Dische et al., J. Biol. Chem. (1951)192:583), that is, 1.1 to 1.7 mkat.

According to another preferred embodiment of the present invention an enteric coated dosage form, selected from the group consisting of enteric coated pellet, enteric coated tablet, enteric coated capsule, enteric coated granules, enteric coated dragees and enteric coated powder, is used and made available for the administration to humans.

According to the invention any kinds of dosage forms may be used, as far as they ensure a quick and effective release of activity at the target. In a preferred embodiment the dosage forms according to the invention may be provided with a coating, more preferred with an enteric coating. These coatings are preferably applied in an amount from 1 to 50% by weight, based on the total weight of the dosage forms. Methacrylic acid/alkyl(meth)acrylate-copolymers are preferred, copolymers of methacrylic acid/methylmethacrylate having a ratio of 1:1 to 1:2, such as Eudragit L® or Eudragit S®, are more preferred and copolymers of methacrylic acid/ethylacrylate 1:1, such as Eudragit L55®, Eudragit L30D-55®, which quickly dissolve at a pH value of >5.5, are most preferred. Furthermore enteric coatings on the basis of celluloses or on the basis of shellac, which are known to the persons skilled in the art, may be applied. The coatings may be applied with suitable solutions or dispersions in organic or aqueous medium, with an aqueous medium being preferred. The enteric coated dosage forms are preferably also resistant to saliva, with coatings on the basis of Eudragit E or Eudragit EPO being suitable.

According to the invention "gastric juice" means the natural composition of the gastric juice as well as the preparations similar to artificial gastric juice, well known to the persons skilled in the art (pH 1-2). Also the term "release in the small intestine" is meant to comprise the release in the natural juice of the small intestine as well as the release in preparations similar to the juice of the small intestine at pH values of 6-7.5, preferably pH 6.4-6.8.

According to the invention "enteric coated" means the characteristic of a dosage form to protect an active ingredient contained therein (e.g., xylose-isomerase) from the action of gastric juice or a solution having comparable properties with gastric juice (e.g., acid) for a determined time period of at least 10, preferably at least 20, more preferred at least 30, most preferred at least 60 minutes in such a way, that the active ingredient is subject to a loss of activity of maximum 50%, preferably of maximum 40%, more preferred of maximum 30%, most preferred of maximum 20%, and in particular of maximum 10%.

The preferred dosage forms are prepared by mixing the starting materials with the enzyme preparation, granulating, extruding, dividing and optionally shaping, preferably spheronizing, optionally classifying, and providing them with an enteric coating.

Enteric coated pellets are pellets enveloped with an enteric coating, which dissolve at a pH value as present in the intestinal tract. I.e., such coatings preferably dissolve at a pH value of at least 4 and maximum 10. Eudragit, for example, an enteric coating based on anionic polymers of methacrylic acid and methacrylates, contains —COOH as functional group and dissolves in the range of pH 5.5 to pH 7. As an alternative to Eudragit shellac or acetylated starch (e.g., Amprac 01) may be used. As the enteric coatings known in the state of the art have different properties (e.g., pH value, at which the coating dissolves, dissolution rate) the materials of the coatings may be combined as well. Shellac, for example, shows a good acid resistance, but dissolves very slowly in the intestinal tract. Amprac 01, on the contrary, dissolves quickly in the intestinal environment, but does not have a sufficient acid resistance. In order to compensate the drawbacks of a material, both of the above mentioned materials may be mixed, for example, in a weight ratio of 60-95/40-5, preferably of 70-90/30-10, shellac/Amprac 01. Another parameter influencing the release rate of the active ingredient is the layer thickness of the enteric coated pellet. The layer thickness, expressed as the mass ratio, is preferably 5 to 30%, more preferred 10 to 20% of the total mass of the final product. The pellets preferably have an average diameter of 0.5 to 5 mm, in particular of 0.7 to 2 mm. Such a size has the advantage that the pellets may pass the stomach quickly.

The preparation of the pellets, which allows for the use of the enzymatic preparation of the invention as drug, food supplement, dietetic food, medicinal product, feeding stuff, supplementary feeding stuff or dietetic feeding stuff, is made preferably using an extruder, which requires a thermal stability of the ingredients of the composition, in particular of the enzymes, up to 60° C. (Stricker Arzneiformenentwicklung, Springer Verlag 2003). The pellets may include further pharmaceutical ingredients in addition to an enteric coating and the enzymes. For example, microcrystalline cellulose (e.g., Avicel) serves as filler and swelling agent. Cellulose is insoluble in water and has in this form crystalline as well as amorphous fractions. This combination causes a plastic deformability, i.e., an irreversible change in shape occurs, if sufficiently force is applied. This is an essential prerequisite for the pelleting in the extruder and spheronizer. During wet granulation microcrystalline cellulose absorbs large quantities of water and therefore becomes an easily compressible, cohesive mass even without the addition of binding agents. The amount of microcrystalline cellulose in a pellet may lie between 5 and 70%, preferably between 10 and 60%, more preferred between 15 and 50%, according to the invention. Maltose may be used as binding agent and filler. Maltose enhances the solubility of the matrix and therefore assists in the rapid release of the enzyme. According to the invention 1 to 40%, preferably 5 to 35%, more preferred 10 to 30% of maltose may be added to one pellet.

As compared with saccharose, which is usually used, maltose has the advantage that it does not include any fructose, and therefore does not introduce any unnecessary and therefore harmful fructose into the body.

Hydroxypropyl cellulose (added in an amount of preferably 0.5 to 10%) may also be added as binding agent, and serves for the avoidance of fine dust. In addition, hydroxypropyl cellulose increases the strength of the pellets and therefore helps to improve the yield. Starch may be added as filler and disintegrant to the pellet of the invention (in a preferred amount of 1 to 30%). As water-insoluble substance, starch may absorb large amounts of water and is therefore an ideal disintegrant. Cross-carmellose (Na-CMC; Acdisol) is a pure disintegrant, which preferably may be added in an amount ranging from 1% to 5%. A too high fraction of Acdisol causes an early disintegration of the pellets already during spheronizing, and is therefore contraproductive. Crosspovidon, a cross-linked PVP, is also insoluble in water and also serves as disintegrant. Based on its polymeric characteristics it promotes a better spheronizing during the preparation of pellets (it may be added preferably in an amount of 0.5 to 10%). Povidon is a water-soluble additive and serves as binding agent. The combination of these different fillers, disintegrants and binding agents results in a molecular disperse distribution of xylose-isomerase in the pellet and ensures a quick bioavailability.

An isolating layer consisting of glycerine and/or talc may be provided between the enteric coating and the pellet including the active ingredient. Glycerine acts as humectant in order to prevent any dehydration and thus inactivation of the enzyme.

As particles having a diameter of more than 3 mm trigger an occlusion reflex at the pylorus, it is in particular preferred that the enteric coated dosage forms, most of all the pellets, leave the stomach with a size of less than 3 mm, as such particles may pass the pylorus in the closed state and may be transported like liquid from the stomach into the small intestine. The neutral pH value prevailing there makes the pellets burst within about 5 to 30 min, preferably 15 min, and thus releases the active substances. Therefore, it is most preferred to provide pellets with less than 5 mm, preferably with less than 3 mm, in diameter as enteric coated dosage form.

As an alternative to pellets, the xylose-isomerase may also be transported in capsules or in a different dosage form through the stomach into the intestinal tract. Suitable capsules are e.g., gelatine capsules or starch capsules. The capsules may also contain the pellets of the invention.

According to a more preferred embodiment of the present invention the xylose-isomerase is present in microcapsules, nanoparticles or liposomes.

According to a preferred embodiment the xylose-isomerase is of microbial, animal, vegetable or recombinant origin.

The enzymes used according to the invention may be of different origins. Methods for the isolation and/or preparation of the enzymes are well known to those skilled in the art.

It is in particular preferred, to use xylose-isomerase of microbial origin, originating from a microorganism of the family of Streptomycetaceae, in particular *Streptomyces rubiginosus*. Xylose-isomerase from sources of this kind have a higher specific activity on glucose/fructose and smaller Km than isomerases of other sources. Thus, xylose-isomerase in *Lactobacillus brevis* has a Km of 920 mM, *Str.rub.* has a Km of 160 mM.

The composition of the invention may be used in the form of different products. Preferably the composition is a pharmaceutical composition, a food supplement, a dietetic food, a medicinal product, a feeding stuff, a supplementary feeding stuff or a dietetic feeding stuff.

Another aspect of the present invention relates to a composition comprising crystalline xylose-isomerase (EC 5.3.1.5) and at least one salt of a metal and/or alkaline earth metal in an enteric coated dosage form, which is in particular selected from the group consisting of enteric coated pellet, enteric coated tablet, enteric coated capsule, enteric coated granules and enteric coated powder.

Another aspect of the present invention relates to the use of xylose-isomerase (EC 5.3.1.5) for the preparation of a drug for the treatment of fructose-malabsorption, where the xylose-isomerase in crystalline form, as described above, is used in drugs. The drug may be, e.g., in an enteric coated dosage form, as defined in the present specification of the invention.

In the case of oral administration of the drug including the xylose-isomerase of the invention should be taken by the consumer immediately before or with each meal containing fructose in order to ensure a quick isomerization. As particles having a diameter of more than 3 mm trigger an occlusion reflex at the pylorus, it is preferred that the enteric coated dosage forms leave the stomach with a size of less than 3 mm, as such particles may pass the pylorus in the closed state and may be transported like liquid from the stomach into the small intestine. The neutral pH value prevailing there makes the pellets burst within about 5 to 30 min, preferably 15 min, and thus releases the active substances.

Another aspect of the present invention relates to a method for the preparation of a composition according to the present invention, comprising the step of crystallizing xylose-isomerase in presence of at least one salt of an alkaline earth metal and/or metal, where the crystalline xylose-isomerase is dried and optionally powdered, and formulated as pharmaceutical dosage form, in particular selected from the group consisting of enteric coated pellet, enteric coated tablet, enteric coated capsule, enteric coated granules and enteric coated powder.

Drying is preferably performed in vacuum and is subdivided into a) filtration of the crystals from the solution and subsequent b) freeze-drying of the filter cake. The dry (residual moisture <5%) filter cake is then preferably ground, for example using a corn mill.

Another aspect of the present invention relates to the composition obtainable by a method according to the present invention.

The present invention will be described in more detail with reference to the accompanying drawings and examples, which, however, should not be considered as limitation.

EXAMPLES

Example 1

Figure 1:
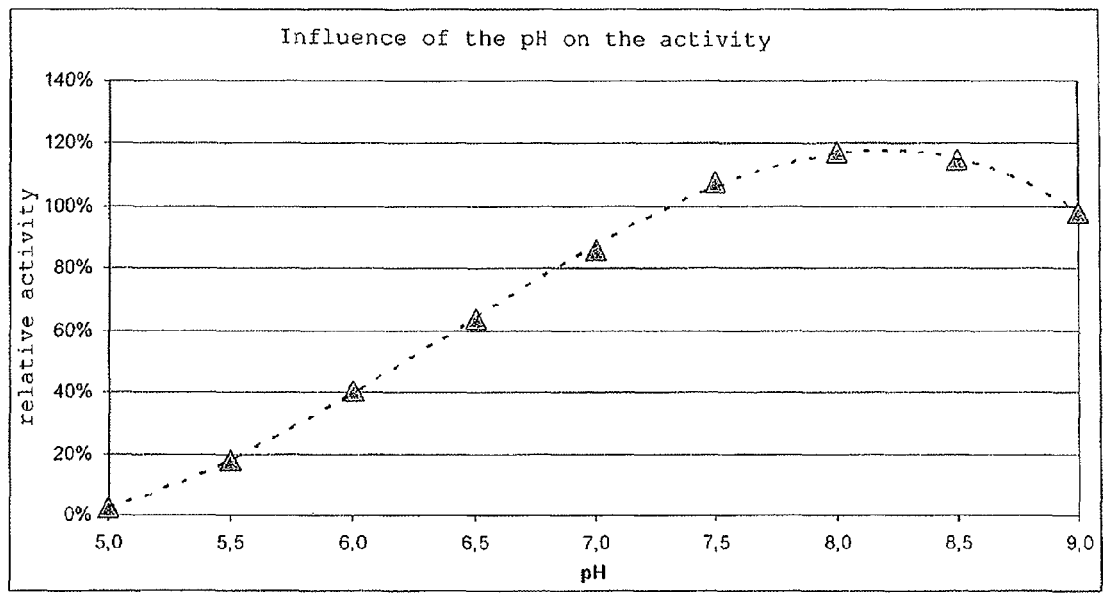
FIG. 1 shows the influence of the pH on the activity of xylose-isomerase.
Figure 2:
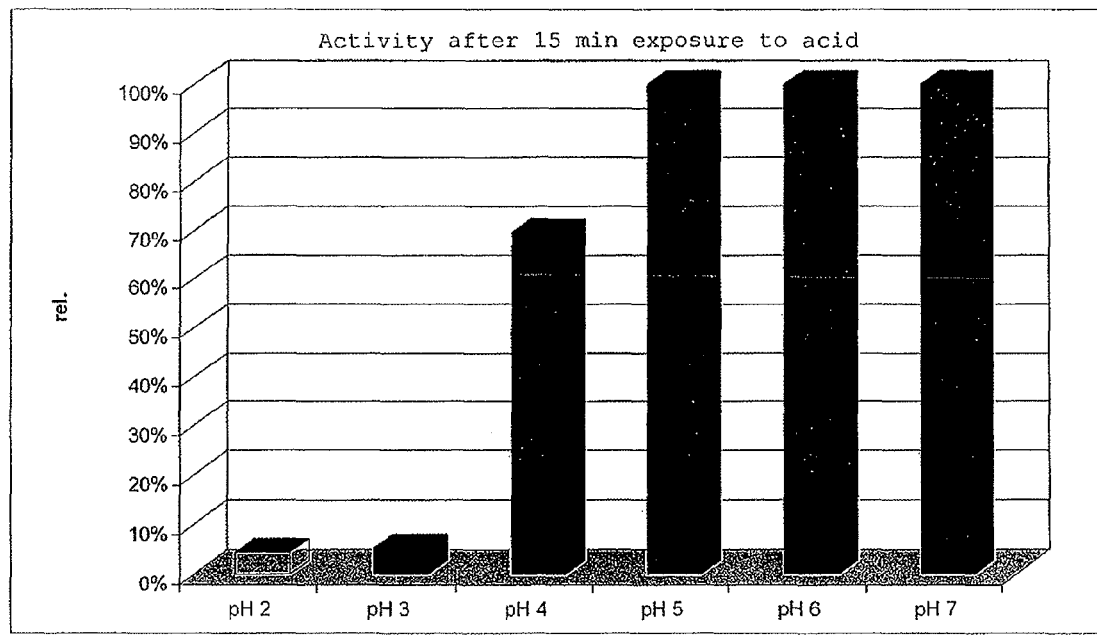
FIG. 2 shows the acid stability of xylose-isomerase. Under conditions of pH<4 the enzyme activity is irreversible destroyed.

In order to ensure a physiologically effective bioavailability in the intestinal region of an individual or animal, it is advantageous to transport xylose-isomerase protected from gastric juice into the small intestine. The determination of the pH dependency of the activity of the enzyme (FIG. 1) and the stability of the enzyme at certain pH values (FIG. 2) serve as the basis for the development of a suitable formulation. The pH dependency of the activity of the glucose isomerase was measured in 50 mM maleate, hepes or Tris-buffer, pH 5 to pH 9, with 5 mM $MgSO_4$, 1 mM $CoCl_2$ and 100 mM glucose at 37° C. The fructose obtained was measured with a modified sulfuric acid/carbazole-test according to Dische and Bohrenfreud (Dische, Z et al.: J Biol Chem. (1951) 192: 583). For the stability a defined amount of enzyme was incubated in 50 mM glycine, maleate or hepes-buffer at a pH of 2 to 7 at 37° C. for 30 min. The buffer was neutralized with an excess of 100 mM hepes buffer, pH 7.4, and the activity was measured in presence of 5 mM $MgSO_4$, 1 mM $CoCl_2$ and 100 mM glucose at 37° C. The fructose obtained was measured with a modified sulfuric acid/carbazole-test according to Dische et al.

Example 2

Figure 3:
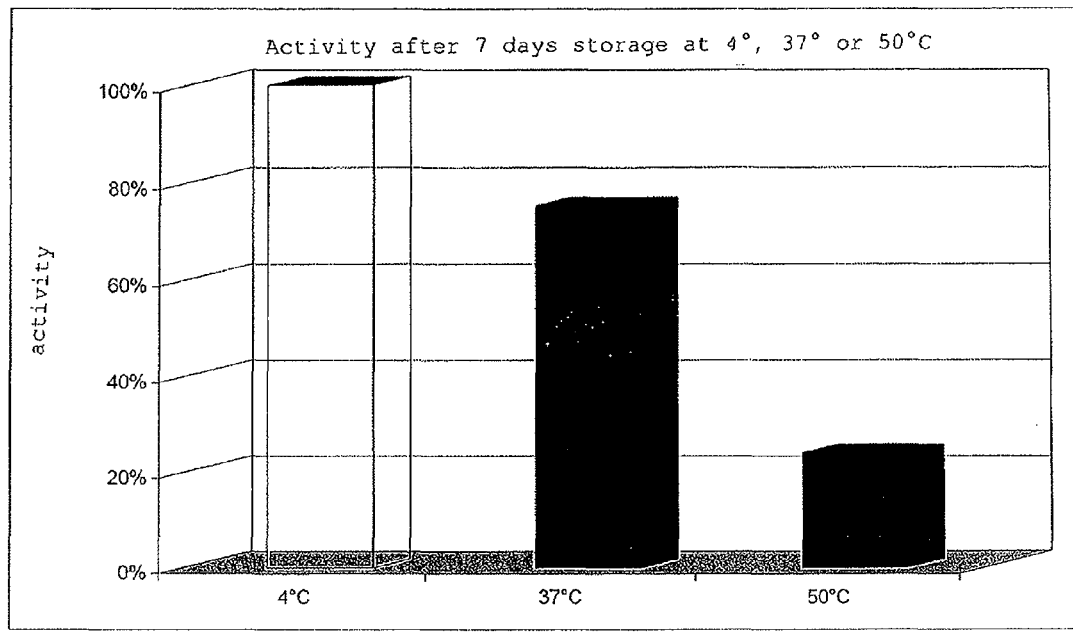
FIG. 3 shows the temperature stability of the activity of the highly active xylose-isomerase of the invention in the preferred embodiment of enteric coated pellets.

Temperature Stability of the Activity of the Highly Active Xylose-Isomerase of the Invention in the Preferred Embodiment of Enteric Coated Pellets The stability of enzyme pellets is of great importance for storage and sale. A sufficient stability of the activity has to be reached, in order to be able to provide an acceptable stability for the market. Coated pellets were stored at 4° C., 37° C. and 50° C. for 7 days and the activity was measured under standard conditions. After 7 days at 37° the activity decreased by 25% and after 7 days at 50° C. by 77% (FIG. 3).

Example 3

Figure 4:
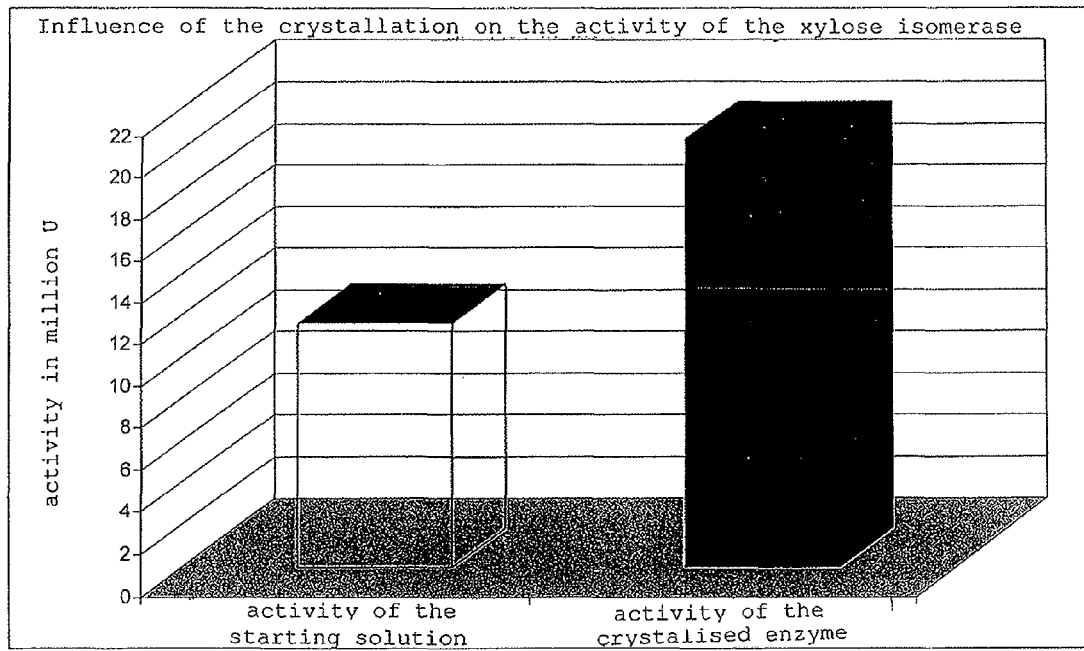
FIG. 4 shows a comparison of the activity of xylose-isomerase purified in a crystallization process with the one of isolated xylose-isomerase.

Comparison of the Activities of Xylose-Isomerase Purified by a Crystallization Process and Isolated Xylose-Isomerase Xylose-isomerase was obtained from *Streptomyces rubiginosus* on a large industrial scale. This acquirable xylose-isomerase was purified by a crystallization process of sorbitol and other additives. Thus, an increase in activity of 70% could be reached. The activity of the crystal suspension obtained in Example 1 and the activity of the starting solution were measured under standard conditions. Here an average increase in activity by 70% was observed (FIG. 4).

Example 4

Influence of Ions of Bivalent Metals on the Activity of Xylose-Isomerase

Figure 5:
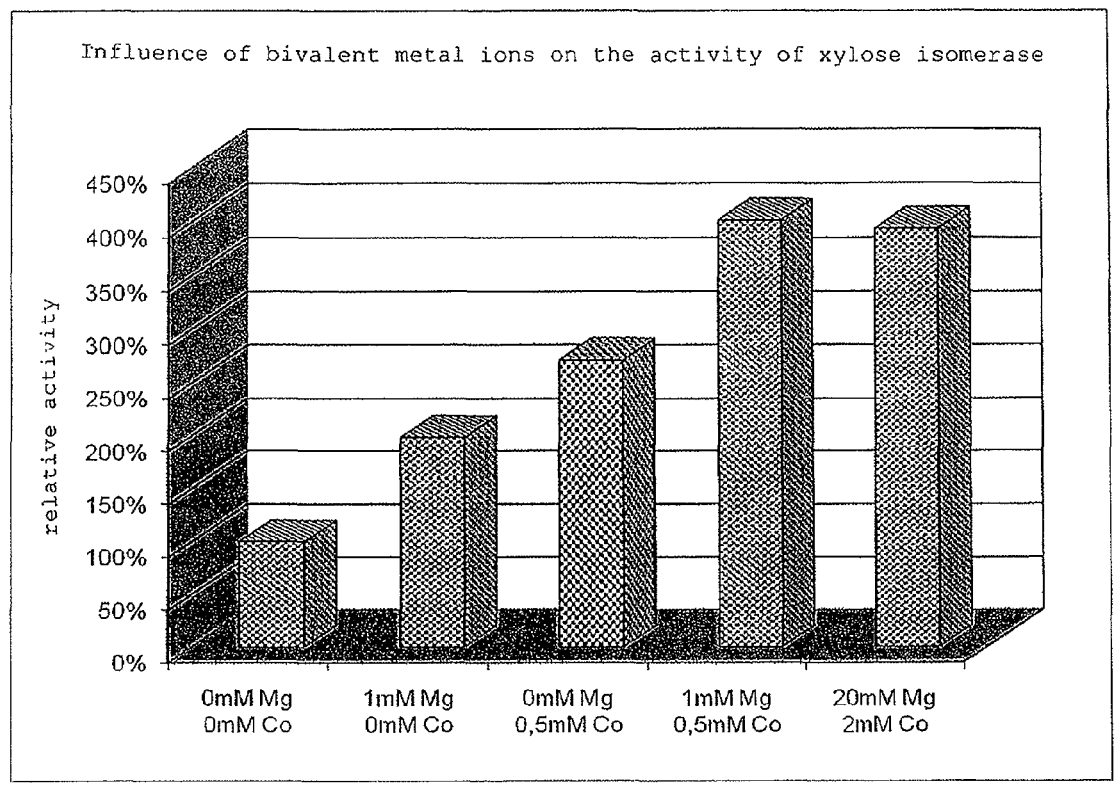
FIG. 5 shows the influence of ions of bivalent metals on the activity of xylose-isomerase.

To xylose-isomerase, purified without addition of bivalent metal ions, different concentrations of $Mg^{2+}$ and $Co^{2+}$ were added and the activity in 50 mM phosphate buffer, pH 7.4, and 100 mM glucose was measured at 37° C. Here an increase in activity by 300% was observed (FIG. 5).

Example 5

Figure 6:
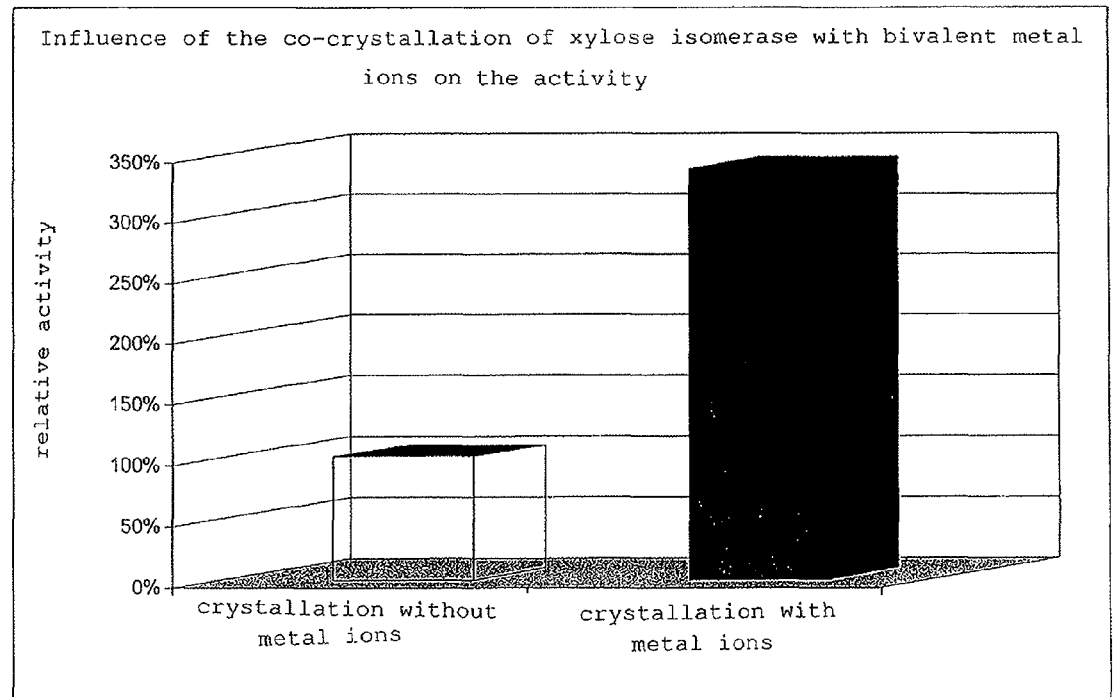
FIG. 6 shows the influence of co-crystallization of xylose-isomerase with bivalent metal ions on the activity of xylose-isomerase.
Figure 7:
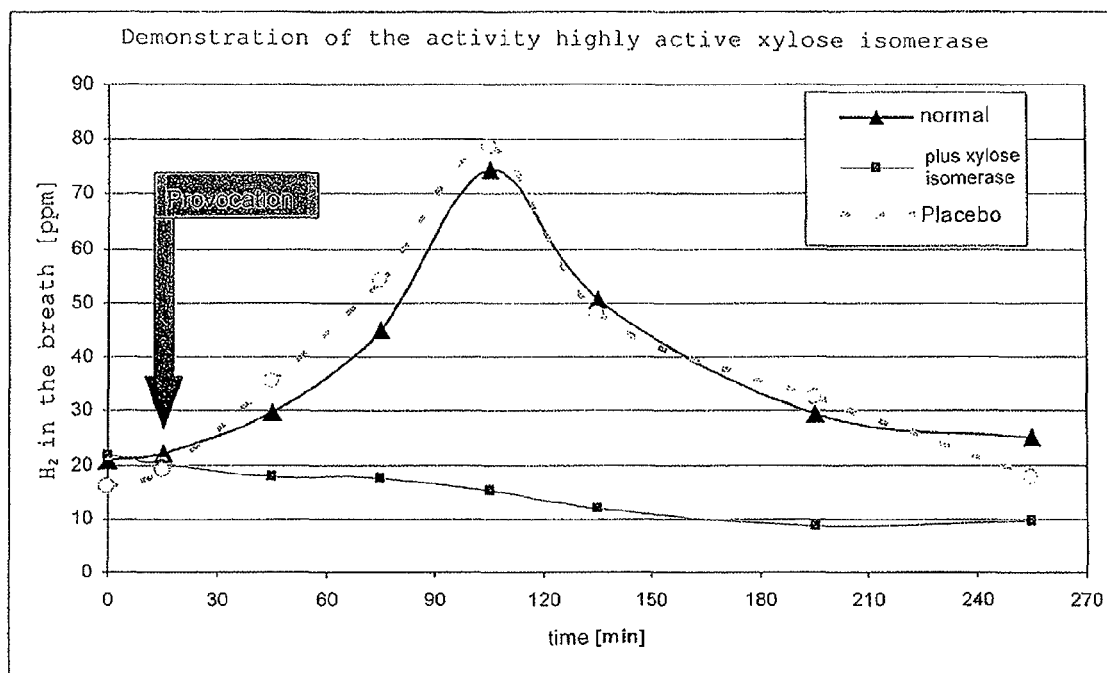
FIG. 7 shows the in vivo effect of xylose-isomerase in the course of time as compared with a placebo and no administration of a substance.

Influence of Co-Crystallization of Xylose-Isomerase with Bivalent Metal Ions on the Activity of the Xylose-Isomerase Xylose-isomerase was crystallized with or without $Mg^{2+}$ and $Co^{2+}$, like in Example 1, and the activity was measured in 50 mM phosphate buffer, pH 7.4, without bivalent metal ions with 100 mM glucose at 37° C. This resulted in a specific activity of the crystals with bivalent metal ions of 300% as compared with crystals without incorporated metal ions (FIG. 6).

Example 6

Crystallization of Xylose-Isomerase in the Presence of Co-Factors

To 5 l of a 4 w/v % xylose-isomerase solution 735 g ammonium sulfate, 72 g magnesium sulfate-hexahydrate and 19.4 g cobalt(II) chloride-hexaydrate were added and slowly cooled down to 2° C. and stirred for 20 hours. In order to accelerate the crystallization process 50 ml of a 4% xylose-isomerase crystal suspension may be added. The resulting crystals should have an optimum size between 50 µm and 100 µm.

This procedure nearly corresponds to the crystallization in U.S. Pat. No. 4,699,882, where, however, $CoCl_2$ and the starter crystals are added.

Example 7

Drying of the Xylose-Isomerase Crystals

The xylose-isomerase crystal suspension obtained in Example 1 is filtered through a pleated filter of class 3hw (Sartorius, Germany). The crystals obtained are frozen and lyophilized. For an optimum processability the solid enzyme cake is finely ground. The xylose-isomerase powder obtained usually has an activity of 45000 units per gram. One unit of xylose-isomerase is defined as the enzymatic activity, which converts 1 µmol (180 µg) of glucose into fructose in 50 mM phosphate buffer, pH7.4, with 5 mM $MgSO_4$, 1 mM $CoCl_2$ and 100 mM glucose at 37° C. (standard conditions) per hour.

Example 8

Preparation of Xylose-Isomerase Pellets a) Granulation:

31.4 g hydroxypropyl cellulose, 408.7 g microcrystalline cellulose, 169.5 g rice starch, 15.6 g croscarmellose, 62.2 g crospovidon, 145.3 g maltose were mixed with 167.1 g xylose-isomerase powder (7,500,000 units). The mixture of solids was processed with 377 g bidistilled water into a wet, crumbly mass. This mass was extruded into strands through a sieve having a pore size of 1 mm (Caleva Extruder 10/25, Caleva Process Solutions Ltd.)

b) Spheronization:

The wet strands were rolled into pellets in a spheronizer (Spheronizer 250, Caleva Process Solutions Ltd.) at 400 rpm for 5 minutes. Then the pellets were dried on racks at 35° C. until the weight was constant.

c) Classification:

The dried pellets were classified in a sieve tube, and the fraction having a size in the range from 0.4 to 0.8 was suitable for further processing.

d) Characterization of the Pellets:

The total yield was 70%.

The release test in the dissolution tester resulted in a release of 85.8% of the activity within 5 minutes and 97.5% of the input activity within 15 minutes into the surrounding environment. By this quick release of the enzyme within a short time a rapid effect is achieved in the gastro-intestinal tract after peroral administration.

e) Coating of the Pellets:

Based on its protein structure, xylose-isomerase is inactivated for the most part in the stomach by pepsin and the acidic pH. Therefore, a protection of the enzyme by an enteric coating or an enteric coated anionic matrix is a prerequisite for the preservation of the enzymatic activity.

Coating solution: 1.9 kg acetylated starch was dissolved in 152 kg purified water while stirring (suspension 1). Using an Ultraturrax, 10.9 kg shellac SSB 63 Hydram was stirred in additional 100 kg purified water to obtain a solution (suspension 2). The suspensions 1 and 2 were mixed and 0.6 kg glycerol 85% and 2.6 kg micronized talc were added. During the spraying procedure the coating solution was stirred with an Ultraturrax.

Coating: 1 kg of pellets was coated with 1.5 kg coating solution in a fluidized bed. The device parameters were selected as follows: spray pressure 1.6 bar, spray rate 180 g/minute, inlet air temperature 55° C., product temperature: 35° C.; inlet air quantity 1400 m$^3$/h.

After application of the complete spraying solution the pellets were re-dried at an inlet air temperature of 40° C. for 60 minutes.

g) Characterization of the Product:

The coated pellets met the test for gastric resistance according to the Pharmacopoea Europaea. After two hours of incubation in the disintegration tester at 37° C. in 0.1 N hydrochloric acid the pellets were unchanged, an exchange of the medium to phosphate buffer pH 6.8 caused the disintegration of the enteric coated pellets within one hour. The coating amounted to about 16% of the original weight. The pellets could also be used as preliminary product for tablets and capsules.

Example 9

Spray Drying of Xylose-Isomerase a) Preparation of the Spraying Solution:

5 g cellulose acetate phthalate was added to 80 g water and the cellulose acetate phthalate was dissolved with aqueous 25% ammonia solution and the pH was adjusted to 7.5. 5 g of an aqueous 100 mM MgSO$_4$ solution was added to the solution and xylose-isomerase crystal suspension, corresponding to a dry mass of enzyme of 1.25 g, was added.

b) Spray Drying:

The following settings were used: inlet temperature 130° C., outlet temperature 90° C., pumping speed 1.5 ml/min, 800 l/h pressurized air and −40 mbar aspiration.

c) Characterization of the Product:

The product yield was 50%. 90% of the activity remained. The xylose-isomerase powder meets the test for gastric resistance according to the Pharmacopoea Europaea. After two hours of incubation in the disintegration tester at 37° C. in 0.1 N of hydrochloric acid the powder was unchanged, an exchange of the medium to phosphate buffer, pH 6.8, resulted in a complete dissolution of the powder within one hour. However, only 5% of the original enzyme activity could be measured in this solution. Therefore the conclusion can be made that while the macroscopic structure of the powder was preserved (as demanded by Pharm Eur), the enzyme activity was lost (which is not a criterion of Pharm Eur).

Example 10

Symptomatic Efficiency

In a clinical study subjects having a diagnosis of fructose-malabsorption were asked to record the individual symptoms in a questionnaire after a certain fructose containing meal. At intervals of about 2 days the same meal should be consumed with increasing numbers of xylose-isomerase containing capsules and the symptom progress should be documented.

Surprisingly the intake of one capsule (=920 units of xylose-isomerase) per meal caused a remarkable improvement of the symptoms, the intake of 2 capsules resulted in a complete disappearance of the symptoms in 75% of the subjects. In further 13% of the subjects the symptoms were reduced.

The average amount of fructose taken per meal in the clinical study was about 7 g. One unit of xylose-isomerase is defined as enzyme quantity, which converts 1 μmol (180 μg) glucose into fructose (and vice versa) at pH 7.4 per hour. This means, that at an average intestinal transit time of one hour 2 capsules degrade a total of 0.33 g of fructose under standard conditions in the laboratory. This value, obtained in the laboratory, lies far below the amount of 7 g taken in the course of the clinical study.

Therefore the special dosage form of highly active xylose-isomerase may dramatically improve the tolerability of fructose, and the short bowel syndrome and related clinical pictures may be successfully treated.

Example 11

Clinical Efficiency 5 persons, who reacted to the provocation of 25 gram of fructose in 100 ml of water with a significant increase in the hydrogen gas content in respiratory air, were administered 3 capsules of the preparation of the invention immediately before the provocation. During the following 4 hours, surprisingly, no increase in the H$_2$-concentration in the respiratory air could be observed. The administration of placebo capsules had no effect on the production of hydrogen gas in the respiratory air. These data confirm that fructose of the highly active xylose-isomerase preparation of the invention taken with meals is converted into glucose while passing the small intestine in such an efficient way that no physiologically relevant amounts of fructose may enter the colon region. 25 g of fructose nearly correspond to the amount, which is daily ingested with food. Therefore, 3 capsules of the preparation of the invention were administered.

The invention claimed is:

1. A method comprising:
obtaining a composition comprising crystalline xylose-isomerase (EC 5.3.1.5) which originates from a microorganism of the family of Streptomycetaceae co-crystallized with a magnesium salt and at least one bivalent metal salt selected from the group consisting of cobalt salt, zinc salt, iron salt and copper salt,
wherein the composition comprises a molar ratio of the bivalent metal salt selected from the group consisting of cobalt salt, zinc salt, iron salt and copper salt to xylose-isomerase ranging from 3:1 to 7:1; and wherein the composition further comprises a molar ratio of the magnesium salt to xylose-isomerase ranging from 5:1 to 200:1; and administering the composition to a subject suffering from symptoms correlated with oral fructose malabsorption.

2. The method of claim 1, wherein the composition is administered in an enteric form.

3. The method of claim 2, wherein the enteric form is further defined as an enteric coated pellet, enteric coated tablet, enteric coated capsule, enteric coated granule, or enteric coated powder.

4. The method of claim 1, wherein the subject is a human with fructose-malabsorption.

5. The method of claim 1, wherein the magnesium salt in the composition has a molar ratio to xylose-isomerase ranging from 5:1 to 25:1.

6. The method of claim 1, wherein the bivalent metal salt selected from the group consisting of cobalt salt, zinc salt, iron salt and copper salt in the composition has a molar ratio to xylose-isomerase ranging from 3:1 to 7:1.

7. The method of claim 1, wherein the magnesium salt is $MgCl_2$, $MgSO_4$, $MgCO_3$, $Mg(HCO_3)_2$, or $Mg(C_4H_2O_4)$.

8. The method of claim 1, wherein the composition is comprised in an enteric-coated dosage form.

9. The method of claim 8, wherein the enteric-coated dosage form is an enteric coated pellet, enteric coated tablet, enteric coated capsule, enteric coated granule, or enteric coated powder.

10. The method of claim 1, wherein the xylose-isomerase is present in microcapsules, nanoparticles, or liposomes.

11. The method of claim 1, wherein the xylose-isomerase of microbial origin originates from *Streptomyces rubiginosus*.

12. The method of claim 1, wherein the composition is a pharmaceutical composition, a food supplement, a dietetic food, a medicinal product, a feeding stuff, a supplementary feeding stuff or a dietetic feeding stuff.

13. The method of claim 1, wherein the at least one bivalent metal salt is selected from the group consisting of $CoCl_2$, $CoSO_4$, $CoCO_3$, $Co(HCO_3)_2$, and $Co(C_4H_2O_4)$.

14. A method of preparing a crystalline enzyme comprising:

co crystallizing xylose-isomerase (EC 5.3.1.5), which originates from a microorganism of the family of Streptomycetaceae with a magnesium salt and at least one bivalent metal salt selected from the group consisting of cobalt salt, zinc salt, iron salt and copper salt, wherein the composition comprises a molar ratio of the bivalent metal salt selected from the group consisting of cobalt salt, zinc salt, iron salt and copper salt to xylose-isomerase ranges from 3:1 to 7:1 and wherein the composition further comprises a molar ratio of the magnesium salt to xylose-isomerase ranges from 5:1 to 200:1.

15. A crystalline xylose-isomerase (EC 5.3.1.5) enzyme, which originates from a microorganism of the family of Streptomycetaceae obtained by co-crystallizing with a magnesium salt and at least one bivalent metal salt selected from the group consisting of cobalt salt, zinc salt, iron salt and copper salt, wherein the composition comprises a molar ratio of the bivalent metal salt selected from the group consisting of cobalt salt, zinc salt, iron salt and copper salt to xylose-isomerase ranging from 3:1 to 7:1 and wherein the composition further comprises a molar ratio of the magnesium salt to xylose-isomerase ranging from 5:1 to 200:1.

* * * * *

UNITED STATES PATENT AND TRADEMARK OFFICE
CERTIFICATE OF CORRECTION

PATENT NO. : 9,144,602 B2  
APPLICATION NO. : 13/062414  
DATED : September 29, 2015  
INVENTOR(S) : Albert Missbichler Page 1 of 1

It is certified that error appears in the above-identified patent and that said Letters Patent is hereby corrected as shown below:

Title Page

On Item (30), line 2, please delete "A 138/2008" and replace with --A 1380/2008-- therefore.

On Item (56), line 10, please delete "EP WO 2007/059956" and replace with --WO 2007/059956-- therefore.

Signed and Sealed this  
Twenty-ninth Day of March, 2016

Michelle K. Lee  
*Director of the United States Patent and Trademark Office*